United States Patent [19]

George et al.

[11] Patent Number: 5,272,157
[45] Date of Patent: Dec. 21, 1993

[54] DERIVATIVES OF 4-(AMINOMETHYL) PIPERIDINE, THEIR PREPARATION AND THEIR THERAPEUTIC APPLICATION

[75] Inventors: Pascal George, St Arnoult-en-Yvelines; Jacques Froissant, Morée; Mireille Sevrin, Paris, all of France

[73] Assignee: Synthelabo, Le Plessis Robinson, France

[21] Appl. No.: 977,869

[22] Filed: Nov. 17, 1992

Related U.S. Application Data

[62] Division of Ser. No. 665,481, Mar. 6, 1991, Pat. No. 5,179,108.

[30] Foreign Application Priority Data

Mar. 7, 1990 [FR] France .................. 90 02855

[51] Int. Cl.[5] .................. C07D 211/26; C07D 211/40; A61K 31/445
[52] U.S. Cl. .................. 514/319; 546/205; 546/206
[58] Field of Search .................. 546/205, 206; 814/319

[56] References Cited

U.S. PATENT DOCUMENTS

| | | | |
|---|---|---|---|
| 3,634,410 | 1/1972 | Nielsen et al. | 260/293.64 |
| 4,357,337 | 11/1982 | Dubroeucz | 546/205 |
| 4,895,841 | 1/1990 | Sugimoto | 514/212 |
| 5,100,901 | 3/1992 | Sugimoto | 514/319 |
| 5,149,714 | 9/1992 | Freedman | 546/206 |
| 5,189,045 | 2/1993 | Peglion | 546/112 |

FOREIGN PATENT DOCUMENTS 224970 9/1991 New Zealand .

OTHER PUBLICATIONS

Bordwell, "Organic Chemistry", McMillan Co., pp. 536–537 (1964).
Solomons, "Organic Chemistry", J. Wiley & Sons, pp. 800–801 (1963).
Myers, "Handbook of Drug and Chemical Stimulation of the Brain", Reinhold Co. pp. 7, 20–21, 80, 435–436, 555–556 (1979).
Chemical Abstracts, vol. 51, No. 1477e (1956).

*Primary Examiner*—C. Warren Ivy
*Assistant Examiner*—Celia Chang
*Attorney, Agent, or Firm*—Jacobson, Price, Holman & Stern

[57] ABSTRACT

Compounds of general formula (I)

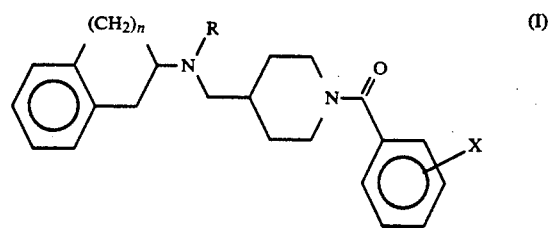

in which
  n is 1 or 2;
  R represents a linear or branched $C_1$–$C_3$-alkyl group; and
  X represents at least one substituent chosen from hydrogen, halogen, $C_1$–$C_3$-alkyl and $C_1$–$C_3$-alkoxy, in the form of a free base or an acid addition salt thereof, and their therapeutic application.

2 Claims, No Drawings

DERIVATIVES OF 4-(AMINOMETHYL) PIPERIDINE, THEIR PREPARATION AND THEIR THERAPEUTIC APPLICATION

This is a division of application Ser. No. 07/665,481, filed Mar. 6, 1991, now U.S. Pat. No. 5,179,108, issued Jan. 12, 1993.

The present invention relates to derivatives of 4-(aminomethyl)piperidine, their preparation and their therapeutic application.

The invention provides a compound which is a 4-(aminomethyl)piperidine derivative of general formula (I)

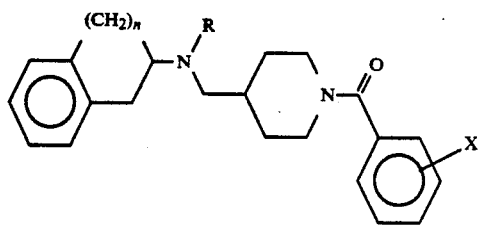

in which
n is 1 or 2;
R represents a linear or branched $C_1$–$C_3$-alkyl group; and
X represents at least one substituent selected from hydrogen, halogen, $C_1$–$C_3$-alkyl and $C_1$–$C_3$-alkoxy; in the form of a free base or an acid addition salt thereof.

In a preferred embodiment of the invention, R is methyl or n-propyl, X is hydrogen, chlorine, methyl, methoxy or ethoxy and any acid addition salt is the hydrochloride.

Examples of specific compounds of the invention are:
4-[N-(indan-2-yl)-N-methyl]aminomethyl-1-benzoyl-piperidine hydrochloride;
4-[N-(indan-2-yl)-N-propyl]aminomethyl-1-benzoyl-piperidine hydrochloride;
4-[N-(1,2,3,4-tetrahydronaphthalen-2-yl)-N-methyl-)aminomethyl-1-benzoylpiperidine hydrochloride; and
4-[N-(1,2,3,4-tetrahydronaphthalen-2-yl)-N-propyl-]aminomethyl-1-benzoylpiperidine hydrochloride.

The invention further provides a process for the preparation of compounds of general formula (I), which comprises reacting a primary amine of general formula (II)

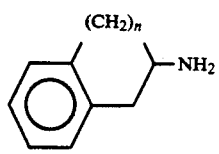

in which n is as hereinbefore defined), which may be in the form of an acid addition salt,
(a) with an alkyl or benzyl chloroformate; or
(b) with a $C_2$ or $C_3$ acid chloride;
reducing the carbamate (a) or the amide (b) thus obtained to give a secondary amine of general formula (III)

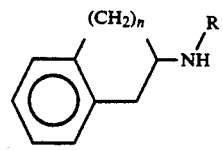

(in which R is as hereinbefore defined), and reacting this secondary amine with a tosylate of general formula (IV)

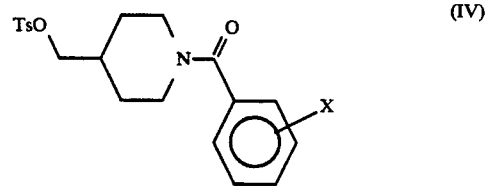

(in which Ts represents a (4-methylphenyl)sulphonyl group and X is as hereinbefore defined), if appropriate in the presence of an organic or inorganic base, and if desired converting a free base of formula I into an acid addition salt.

The process of the invention is illustrated by the reaction scheme given below:

Reaction Scheme

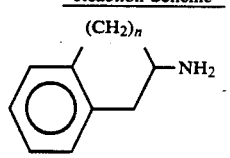

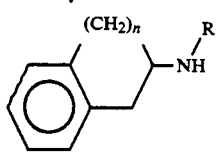

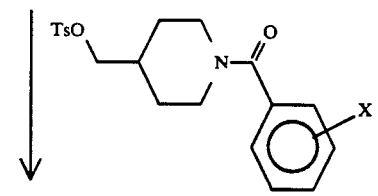

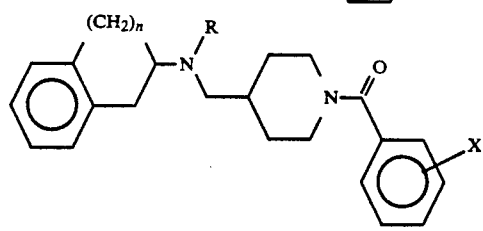

Steps (a) and (b) may be carried out in an inert aprotic solvent such as toluene, tetrahydrofuran, or a halogenated solvent, for example dichloromethane, and in the presence of an organic base such as a tertiary amine, for example triethylamine.

In the first case (a), an alkyl or benzyl carbamate is obtained which, by means of reduction, for example with lithium aluminium hydride, in an ethereal solvent such as tetrahydrofuran, gives a secondary amine of general formula (III) in which R represents a methyl group. In the second case (b), an amide is obtained which, by reduction, for example with lithium aluminium hydride, in an ethereal solvent such as tetrahydrofuran, gives a secondary amine of general formula (III) in which R represents a $C_2$ or $C_3$ alkyl group.

The secondary amine (III) is then reacted with a tosylate of formula (IV) (in which Ts represents a (4-methylphenyl)sulphonyl group), optionally in the presence of an inert solvent such as dimethylformamide, toluene or xylene, at a temperature of 20° to 150° C., and if appropriate in the presence of an organic base, such as a tertiary amine, or inorganic base, such as an alkali metal carbonate or hydrogen-carbonate.

The starting amine of general formula (II) in which $n=1$ is commercially available (2-aminoindan); the starting amine of general formula (II) in which $n=2$ can be prepared according to known methods, starting from 3,4-dihydro(1H)naphthalen-2-one, which is commercially available, by reaction with hydroxylamine hydrochloride in the presence of sodium acetate, then catalytic hydrogenation of the intermediate oxime.

The tosylate of formula (IV) can be prepared, for example, as described in EP-A-0,306,375.

The following Examples illustrate in detail the preparation of some compounds according to the invention. The elemental microanalyses and the IR and NMR spectra confirm the structures of the products obtained.

EXAMPLE 1

4-[N-(indan-2-yl)-N-methyl]aminomethyl-1-benzoylpiperidine hydrochloride a) Ethyl indan-2-carbamate 200 ml of dichloromethane then 10 ml, i.e. 7.26 g (71.7 mmol) of triethylamine were added to 5 g (29.5 mmol) of 2-aminoindan hydrochloride. The mixture was stirred for 30 min, then 3.4 ml, i.e. 3.84 g (35.4 mmol) of ethyl chloroformate were added dropwise. The mixture was stirred for 30 min, then ice-water and an excess of 1N hydrochloric acid were added. The precipitate was filtered, washed, dried and purified by chromatography on a silica gel column, eluted with an 80:20 mixture of dichloromethane/ethyl acetate. 4.25 g of amorphous solid were isolated.

Melting point: 68°–68.5° C.

b) 2-(N-methyl)aminoindan

To a suspension of 1.13 g (30 mmol) of anhydrous lithium aluminium hydride in 150 ml of tetrahydrofuran was added a solution of 2.2 g of ethyl indan-2-carbamate in 50 ml of the same solvent. The mixture was heated to reflux, allowed to cool, hydrolysed with an excess of aqueous 1N sodium hydroxide solution, and the mixture was filtered, concentrated and distilled at about 100 Pa at 150° C. 3.5 g of oil were obtained.

c) 4-[N-(indan-2-yl)-N-methyl]aminomethyl-1-benzoylpiperidine hydrochloride

A mixture of 1.13 g (7.7 mmol) of 2-(N-methyl)aminoindan and 2.9 g (7.7 mmol) of (1-benzoylpiperidin-4-yl)methyl 4-methylphenylsulphonate was heated under nitrogen in a 50 ml flask in an oil bath at 150° C. for 3 h. The mixture was allowed to return to room temperature, and dichloromethane and an excess of aqueous 1N sodium hydroxide solution were added. After the reaction medium had completely dissolved, the organic phase was separated, the solvent was evaporated and the residue was purified by chromatography on a silica gel column, eluted with a 97:3 mixture of dichloromethane/methanol. 1.3 g of amide were obtained, to which was added 3 ml of 1.7M hydrochloric acid in ethanol, the mixture was stirred for 15 min and evaporated to dryness, and the solid was recrystallised in acetonitrile and then in acetone. 0.95 g of hydrochloride were finally isolated.

Melting point: 212°–213° C.

EXAMPLE 2

4-[N-(indan-2-yl)-N-propyl)aminomethyl-1-benzoylpiperidine hydrochloride a) N-(indan-2-yl)propionamide 200 ml of dichloromethane, then 15 ml, i.e. 10.9 g (107.6 mmol) of triethylamine were added to 5 g (29.5 mmol) of 2-aminoindan hydrochloride. The mixture was stirred, then 2.6 ml (29.5 mmol) of propionyl chloride were added and stirring was continued at room temperature for 12 h. Dilute hydrochloric acid was added, the precipitate was filtered, washed, dried and purified by chromatography on a silica gel column, eluted with an 80:20 mixture of dichloromethane/ethyl acetate. 4.87 g of beige solid were isolated.

b) 2-(N-propyl)aminoindan

Under the conditions described in connection with 2-(N-methyl)aminoindan, 4.87 g (25.7 mmol) of N-(indan-2-yl)propionamide in tetrahydrofuran were reduced by means of 1.95 g (51.4 mmol) of lithium aluminium hydride. After distillation ($\approx$100 Pa, 135° C.), 4.22 g of amine were obtained.

c) 4-[N-(indan-2-yl)-N-propyl]aminomethyl-1-benzoylpiperidine hydrochloride

A mixture of 2.28 g (13 mmol) of 2-(N-propyl)aminoindan and 5.0 g (14.4 mmol) of (1-benzoylpiperidin-4-yl)methyl 4-methylsulphonate was heated at 170° C. for 2 h. The mixture was allowed to return to room temperature, and dichloromethane and an excess of aqueous 1N sodium hydroxide solution were added. After the reaction medium had dissolved completely, the organic phase was separated, the solvent was evaporated and the residue was purified by chromatography on a silica gel column, eluted with a 97:3 mixture of dichloromethane/methanol. 1.48 g of viscous oil were obtained. 2.3 ml of 1.7M hydrochloric acid in ethanol were added, the mixture was stirred for 30 min and evaporated to dryness, and the solid was recrystallised in acetone. 0.61 g of hydrochloride were finally isolated.

Melting point: 174°–176° C.

EXAMPLE 3

4-[N-(1,2,3,4-tetrahydronaphthalen-2-yl)-N-methyl]aminomethyl-1-benzoylpiperidine hydrochloride a) 3,4-dihydro(1H)naphthalene-2-oxime A mixture of 12.34 g (84.4 mmol) of 3,4-dihydro(1H)naphthalen-2-one, 15.13 g (184.4 mmol) of sodium acetate and 9.97 g (143.5 mmol) of hydroxylamine hydrochloride in 250 ml of absolute ethanol was heated to reflux for 1 h. The mixture was concentrated, water and diethyl ether were added, the organic phase was separated, washed with water and dried over sodium sulphate, and the solvent was evaporated. 13.45 g of orange oil were obtained.

b) 2-amino-1,2,3,4-tetrahydronaphthalene hydrochloride 55 ml of 1.7M ethanolic hydrogen chloride, 5 ml of chloroform and 0.3 g of platinum oxide were added to 13.45 g (83.4 mmol) of 3,4-dihydro-(1H)naphthalene-2-oxime, and the mixture was stirred, then subjected to hydrogenation under a pressure of about 0.31 MPa at room temperature for 4 h, then at 35° C. for 10 h. The mixture was filtered, the filtrate was partly evaporated and the white solid which precipitated was filtered. After drying 3.22 g of hydrochloride were obtained.

c) Phenylmethyl 1,2,3,4-tetrahydronaphthalene-2-carbamate

A mixture of 11.0 g of 2-amino-1,2,3,4-tetrahydronaphthalene hydrochloride, 200 ml of dichloromethane and 17.6 ml, i.e. 12.8 g (126 mmol) of triethylamine was stirred for 30 min. 10.3 ml (72.2 mmol) of phenylmethyl chloroformate were then added slowly, and stirring was continued for 12 h. Ice-water and an excess of 1N hydrochloric acid were added. The precipitate was filtered, washed, dried and purified by chromatography on a column of silica gel, eluted with an 80:20 mixture of dichloromethane/ethyl acetate. 12.3 g of carbamate were isolated.

d) 2-(N-methyl)amino-1,2,3,4-tetrahydronaphthalene 7.43 g (26.4 mmol) of phenylmethyl 1,2,3,4-tetrahydronaphthalene-2-carbamate were added in portions to a suspension of 4.5 g (26.4 mmol) of lithium aluminium hydride in 200 ml of tetrahydrofuran, and the mixture was heated to reflux for 3 h 30, allowed to cool, and hydrolysed with an excess of aqueous 1N sodium hydroxide solution, the mixture was filtered and concentrated, and the residue was distilled at about 80 Pa between 140 and 240° C. 4.78 g of impure oil were obtained, which was utilised in its impure state in the following step.

e) 4-[N-(1,2,3,4-tetrahydronaphthalen-2-yl)-N-methyl]aminomethyl-1-benzoylpiperidine hydrochloride 10.7 g (32 mmol) of (1-benzoylpiperidin-4-yl)methyl 4-methylphenylsulphonate were added to 4.78 g of the amine obtained above and the mixture was heated in an oil bath at 140° C. for 3 h. The mixture was allowed to return to room temperature, and dichloromethane and an excess of aqueous 1N sodium hydroxide solution were added. After the reaction medium had dissolved completely, the organic phase was separated, the solvent was evaporated and the residue was purified by chromatography on a silica gel column, eluted with a 97:3 mixture of dichloromethane/methanol. 4.02 g of still impure material were obtained, to which 7 ml of 1.7M hydrochloric acid in ethanol were added, the mixture was stirred for 30 min and evaporated to dryness, and the solid was recrystallised in a mixture of toluene and acetonitrile, then in acetone. 0.84 g of white crystalline hydrochloride were finally isolated.

Melting point: 223°-225° C.

EXAMPLE 4

4-[N-(1,2,3,4-tetrahydronaphthalen-2-yl)-N-propyl]aminomethyl-1-benzoylpiperidine hydrochloride Working as in Example 3, but using 2-(N-propyl)amino-1,2,3,4-tetrahydronaphthalene as the amine of general formula (III) (prepared from 2-amino-1,2,3,4-tetrahydronaphthalene hydrochloride, according to the method described in Example 2, a and b), 4-[N-(1,2,3,4-tetrahydronaphthalen-2-yl)-N-propyl]aminomethyl-1-benzoylpiperidine hydrochloride was obtained.

Melting point: 200°-202° C.

The table which follows illustrates the chemical structures and the physical properties of some compounds according to the invention.

TABLE

| No. | n | R | X | Salt | M.p. (°C.) |
|---|---|---|---|---|---|
| 1 | 1 | $CH_3$ | H | HCl | 212-213 |
| 2 | 1 | $nC_3H_7$ | H | HCl | 174-176 |
| 3 | 2 | $CH_3$ | H | HCl | 223-225 |
| 4 | 2 | $nC_3H_7$ | H | HCl | 200-202 |
| 5 | 1 | $nC_3H_7$ | 4-F | HCl | 190-192 |
| 6 | 1 | $nC_3H_7$ | 3-Cl | HCl | 151-154 |
| 7 | 1 | $nC_3H_7$ | 3-$CH_3$ | HCl | 147-148 |
| 8 | 1 | $nC_3H_7$ | 3-$OCH_3$ | HCl | 188-190 |
| 9 | 1 | $nC_3H_7$ | 3-$OC_2H_5$ | HCl | 200-203 |

Note: In the column "R", "$nC_3H_7$" denotes an n-propyl group; in the column "salt", "HCl" denotes a hydrochloride.

The compounds of the invention have been submitted to a series of pharmacological tests which have revealed their utility as therapeutically active substances.

They have been the subject of a study with regard to their affinity for serotoninergic receptors of the 5-$HT_{1A}$ type present in the hippocampus of the rat. The compounds displace the binding of a specific labelled ligand, [$^3H$]-8-hydroxy-2-di-n-propylaminotetralin (designated below by "[$^3H$]-8-OH-DPAT" and described by Gozlan et al., Nature, (1983), 305, 140-142) on the 5-$HT_{1A}$ receptors. The animals used were male Sprague-Dawley rats weighing 160 to 200 g. After decapitation, the brain was removed and the hippocampus was dissected out. The tissue was ground in an Ultra-Turrax Polytron ® apparatus for 30 s at half the maximum speed in 10 volumes of 50 mM tris buffer adjusted to pH 7.4 with hydrochloric acid (i.e. 100 mg of fresh tissue per ml). The homogenised tissues were washed twice at 4° C., by centrifuging them at 48,000×g for 10 min each time and resuspending the pellets in fresh cold buffer. Finally, the last pellet was suspended in the buffer to give a concentration of 50 mg of starting tissue per ml of 50 mM buffer. The mixture was then incubated at 37° C. for 10 min.

The binding to [$^3H$]-8-OH-DPAT (1 nM) was determined by incubation of 50 μl of membrane suspension in a final volume of 250 μl of buffer containing 10 μM pargyline and 3 μM paroxetine. After incubation at 37° C. for 15 min, the membranes were recovered by filtration on Whatman GF/B ® filters which were washed three times with aliquot quantities of 5 ml of iced buffer. The filters were extracted in the scintillation liquid and the radioactivity was measured by liquid scintigraphy. The specific binding of [$^3H$]-8-OH-DPAT was defined as the quantity of radioactive material retained on the filters and being able to be inhibited by co-incubation in 10 μM 5-hydroxytryptamine. At a concentration of 1 nM [$^3H$]-8-OH-DPAT, the specific binding represented 90% of the total radioactivity recovered on the filter.

For each concentration of compound studied, the percentage inhibition of binding with [$^3$H]-8-OH-DPAT was determined, then the concentration IC$_{50}$, the concentration which inhibits 50% of the binding.

For the compounds of the invention, the IC$_{50}$ lie between 0.001 and 0.1 μM.

The central activity of the compounds of the invention was evaluated by their effects on the "PGO (pontogeniculo-occipital) spikes" induced by reserpine in the cat, according to the method described by H. Depoortere in Sleep 1976, 3rd Europ. Congr. Sleep Res., Montpellier 1976, 358–361 (Karger, Basel 1977).

Cumulative doses of the compounds to be studied (from 0.001 to 3 mg/kg intravenously) were administered at intervals of 30 min, 4 h after intraperitoneal injection of a dose of 0.75 mg/kg of reserpine, to curarised cats under artificial ventilation. The electroencephalographic and phasic activities (PGO-R spikes) were recorded with the aid of cortical and deep (lateral geniculate) electrodes. For each dose of the compound studied, the percentage decrease in the number of PGO spikes, then the AD$_{50}$, the active dose which decreases this number of spikes by 50%, were determined. For the compounds of the invention, the intravenous AD$_{50}$ values lie between 0.001 and 1 mg/kg.

The results of the tests show that the compounds of the formula (I) possess, in vitro, a high affinity and a selectivity for 5-HT$_{1A}$ type serotoninergic receptors. In vivo, they show an agonist, partial agonist or antagonist activity, at these receptors.

The compounds of the invention may therefore be used for the treatment of diseases and conditions directly or indirectly involving the 5-HT$_{1A}$ type serotoninergic receptors, especially for the treatment of depressive states, anxiety states, sleep disorders, for the regulation of food intake, for the treatment or the prevention of vomiting and of motion sickness, and also for the treatment of vascular or cardiovascular disorders such as migraine and hypertension.

To this end, they can be formulated as pharmaceutical compositions in which they are the active ingredient. They can be presented in all forms appropriate to their administration orally or parenterally, in combination with all suitable excipients, and in doses permitting a daily dosage of 1 to 1,000 mg.

We claim:

1. A compound which is a 4-(aminomethyl) piperidine derivative of formula (I)

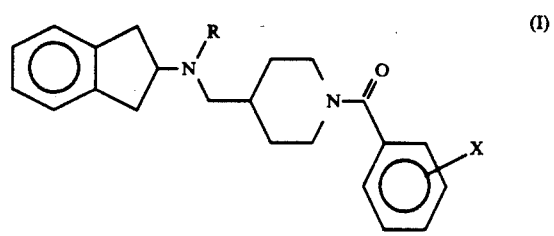

in which
R represents a linear or branched C$_1$–C$_3$-alkyl group; and
X represents one substituent selected from hydrogen, halogen, C$_1$–C$_3$-alkyl and C$_1$–C$_3$-alkoxy;
in the form of a free base or an acid addition salt thereof.

2. A compound according to claim 1, which is:
4-[N-(indan-2-yl)-N-methyl]aminomethyl-1-benzoyl-piperidine hydrochloride; or
4-[N-(indan-2-yl)-N-propyl]aminomethyl-1-benzoyl-piperidine hydrochloride.

* * * * *